(12) United States Patent
Borzatta et al.

(10) Patent No.: US 7,019,154 B2
(45) Date of Patent: Mar. 28, 2006

(54) PROCESS FOR THE PRODUCTION OF 5-BENZYL-3-FURFURYL ALCOHOL

(75) Inventors: Valerio Borzatta, Bologna (IT); Dario Brancaleoni, Sasso Marconi (IT); Goffredo Rosini, Bologna (IT); Lucilla D'Adamo, Vasto (IT)

(73) Assignee: Endura S.p.A., Bologna (IT)

( * ) Notice: Subject to any disclaimer, the term of this patent is extended or adjusted under 35 U.S.C. 154(b) by 287 days.

(21) Appl. No.: 10/476,528

(22) PCT Filed: Apr. 25, 2002

(86) PCT No.: PCT/EP02/04576

§ 371 (c)(1),
(2), (4) Date: Oct. 29, 2003

(87) PCT Pub. No.: WO02/090341

PCT Pub. Date: Nov. 14, 2002

(65) Prior Publication Data

US 2004/0127728 A1    Jul. 1, 2004

(30) Foreign Application Priority Data

May 4, 2001    (IT) ........................... MI2001A0914

(51) Int. Cl.
   *C07D 307/02*    (2006.01)

(52) U.S. Cl. ..................................................... 549/497
(58) Field of Classification Search ................. 549/497
   See application file for complete search history.

(56) References Cited

OTHER PUBLICATIONS

Database Crossfire Beilstein 'Online!, Beilstein Institut zur Förderung der Chemischen Wissenschaften, Frankfurt am Main, DE; Database accession No. 139508, XP002213661, Abstract, & Mnoshojan, Afrikjan: Dokl. Akad. Nauk. Arm. Ssr. vol. 25, 1957, p. 201.

Mimi L. Quan et al., "Design and Synthesis of Isoxazoline Derivatives as Factor Xa Inhibitors," J. Med. Chem., vol. 42, No. 15 1999, pp. 2760-2773, XP002213660.

*Primary Examiner*—Kamal A. Saeed
*Assistant Examiner*—Robert Shiao
(74) *Attorney, Agent, or Firm*—Nixon Peabody LLP

(57) ABSTRACT

Synthesis process of 5-benzyl-3-furfuryl alcohol including the reduction reaction with $NaBH_4$ or with sodium dihydro bis-(2-methoxyethoxy)aluminium hydride of 3-benzyl-5-hydroxymethyl-5-carboxyalkyl isoxazoline to give 3-benzyl-5,5-bis(hydroxymethyl)isoxazoline which, through subsequent reduction in the presence of a weak protic acid and consequent rearrangement with strong aqueous acid, gives 5-benzyl-3-furfuryl alcohol.

35 Claims, 1 Drawing Sheet

PROCESS FOR THE PRODUCTION OF 5-BENZYL-3-FURFURYL ALCOHOL

FIELD OF THE INVENTION

The present invention concerns a synthesis process of 5-benzyl-3-furfuryl alcohol.

PRIOR ART

Synthesis processes of 5-benzyl-3-furfuryl alcohol are well known to the art, an intermediate through the synthesis of the pyrethroid type of insecticide known by its commercial name of Resmethrin and described, for instance, in GB 1,168,797. For instance the patent U.S. Pat. No. 3,466,304 claims the synthesis of 5-benzyl-3-furfuryl alcohol through condensation of Claisen of benzylcyanide and dialkylsuccinate, consequent hydrolysis, esterification, protection of the ketone group, formylation, cyclization to 5-benzyl-3-furfuryl ester and subsequent reduction to alcohol with lithium aluminium hydride.

The process is particularly laborious, it requires anhydrous solvents and uses Lithium aluminium hydride the handling of which requires numerous precautions. The patent EP 187 345 claims a procedure for the synthesis of substituted furanes by substituted isoxazolidine obtained from isobutylene diacetate and the appropriate aldoxime. The process envisages, therefore, the use of isobutylene diacetates, obtained from dichloroisobutylenes, or of dihydroxy isobutylenes which are difficult to prepare and find (DE 3,243,543 and DE 3,415,336).

The patent SU 1768601 claims the synthesis of 5-benzyl-3-furfuryl alcohol through reduction of the corresponding ester with Lithium aluminium hydride. The furane ester is obtained through the condensation of 2-benzylfurane with an alkyl ester of propiolic acid at 200–250° C. in autoclave.

The conditions described by way of example are demanding or as such to be hardly exploited in industrial-scale plants.

The need was therefore felt to realize new ways of synthesis with reactions characterized by high yields, easily to be scaled up to industrial size, with intermediates of high degree of purity, by using reagents commercially available.

SUMMARY

A new synthesis process of 5-benzyl-3-furfuryl alcohol has now been found which is able to overcome the drawbacks typical of the processes known to the art.

The Applicant has unexpectedly and surprisingly found a new synthesis process of 5-benzyl-3-furfuryl alcohol comprising:

a. Condensation of the alkyl α-(hydroxymethyl)acrylate, obtained through a Witting-Horner type reaction of a alkyl phosphonate with formaldehyde, with phenyl acetaldehyde oxime in the presence of an aqueous solution of sodium hypochlorite to give 3-benzyl-5-hydroxymethyl-5-carboxyalkyl isoxazoline.
b. Reduction of the 3-benzyl-5-hydroxymethyl-5-carboxyalkyl isoxazoline with sodium borohydride or with sodium dihydro-bis-(2-methoxyethoxy)aluminium hydride to give 3-benzyl-5,5-bis(hydroxymethyl)isoxazoline.
c. Hydrogenation and consequent rearrangement of 3-benzyl-5,5-bis(hydroxymethyl)isoxazoline to give 3-benzyl-5-furfuryl alcohol.

The process under discussion is characterized by few steps of easy industrial applicability and high yield, starting with reagents easily found on the market, of reasonable cost and safer to handle compared to the raw materials pointed out in the known art among which, in particular, the difficult to find and expensive dichloro or dihydroxy isobutylene, (*Organic Syntheses* Vol.75, pages 89–97 (1997)).

DETAILED DESCRIPTION OF THE INVENTION

Figure 1:
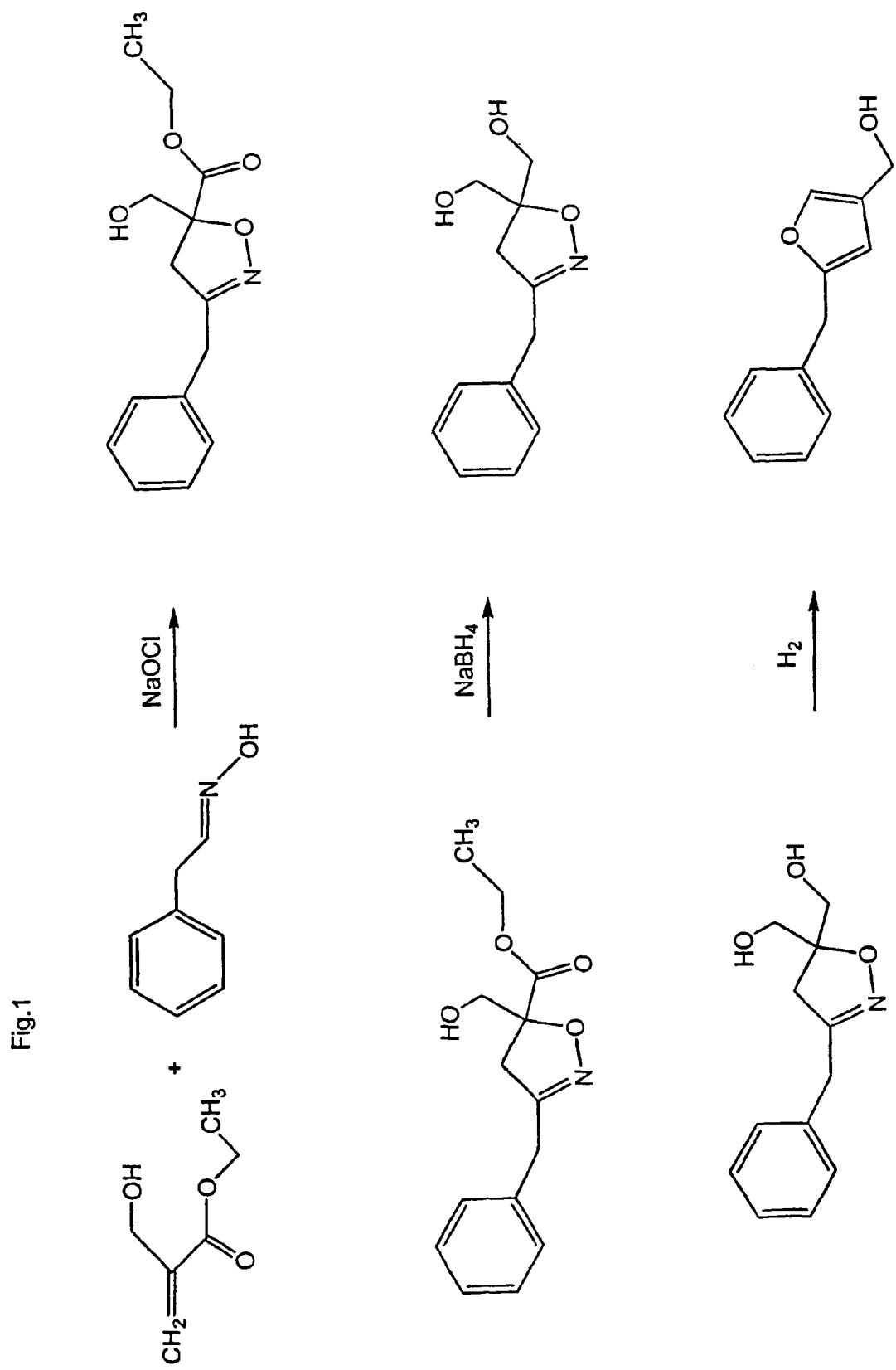
FIG. 1: scheme of the synthesis of 5-benzyl-2-hydroxymethyl furane alcohol.

It is an object of the present invention a synthesis process of 5-benzyl-3-furfuryl alcohol comprising the following steps:
a) condensation reaction of the alkyl ($C_1$–$C_4$) alpha-(hydroxymethyl)acrylate with phenylacetaldehyde oxime in the presence of sodium hypochlorite (NaOCl) to give 3-benzyl-5-hydroxymethyl-5-carboxymethyl isoxazoline;
b) reduction reaction with sodium borohydride ($NaBH_4$) or sodium dihydro-bis-(2-methoxyethoxy)aluminium hydride ($NaAlH_2(OCH_2CH_2OCH_3)_2$) of 3-benzyl-5-hydroxymethyl-5-carboxymethyl isoxazoline to give 3-benzyl-5,5-bis(hydroxymethyl)isoxazoline;
c) catalytic hydrogenation reaction of 3-benzyl-5,5-bis(hydroxymethyl)isoxazoline and consequent rearrangement to give 5-benzyl-3-furfuryl alcohol.

According to the synthesis process of the present invention, the condensation reaction of step a) is preferably carried out in aromatic or aliphatic halogenated solvents.

The aliphatic halogenated solvents and particularly the chlorinated ones of 1 to 2 carbon atoms are the most preferred. Methylene chloride is particularly preferred. The technique is carried out at a temperature of between –10° C. and 80° C.; the range between –10° C. and 50° C. is preferred; temperature between –10° C. and 30° C. is particularly preferred.

The condensation reaction at step a) is carried out in the presence of an aqueous solution of sodium hypochlorite with an active chlorine titre of between 5 and 10% p/p. A titre of between 8 and 10% p/p is preferred. A titre of 10% p/p is particularly preferred.

The reduction reaction at step b) with sodium borohydride is carried out in a $C_1$–$C_4$ aliphatic alcohol or mixtures thereof, methyl alcohol is particularly preferred; when sodium dihydro bis-(2-methoxyethoxy)aluminium hydride is used, the reaction is carried out in aliphatic or aromatic solvents selected from the group consisting of benzene, toluene, xylene, cyclohexane, methylcyclohexane or mixtures thereof. Toluene is particularly preferred.

The temperature of the reduction reaction at step b) is between –15° C. and 30° C.; the range from –10° C. to 25° C. is preferred.

The reduction reaction is preferably carried out with sodium borohydride granules (10–40 mesh) in methanol or sodium dihydro-bis-(2-methoxyethoxy)aluminium hydride in toluene, for the latter case a 70% p/p solution, in toluene, of sodium dihydro-bis-(2-methoxyethoxy)aluminium hydride (Synhydrid®) is particularly preferred.

The hydrogenation reaction at step c) is carried out at a hydrogen pressure of between 0.5 and 40 bar; a range between 1 and 20 bar is preferred; the range between 1 and 10 bar is particularly preferred.

The temperature of hydrogenation is between 15° C. and 100° C.; the range between 20° C. and 60° C. is preferred.

The catalysts used in the hydrogenation reaction are those commonly used for catalytic hydrogenation, as such or supported on the appropriate inert matrix. Typical examples of catalysts are $PtO_2$, PtO, Ni Raney, Pt on carbon, Pd on carbon, Pd on $BaSO_4$, Pd on $Al_2O_3$, Pt on $Al_2O_3$, Ru on carbon.

Pd on carbon, $PtO_2$ and Ni Raney are preferred. Ni Raney is particularly preferred. The hydrogenation reaction at step c) is carried out in a $C_1$–$C_4$ alcoholic solvent or mixtures thereof, or in hydroalcoholic mixtures of said $C_1$–$C_4$ alcohols, the quantity of water of said mixtures ranging from 7 to 50% v/v of the solution.

Methanol is preferred as the alcohol.

A methanol/water mixture is preferred with a quantity of water from 10 to 30% v/v. A methanol/water mixture containing from 15% to 20% v/v of water is particularly preferred.

The hydrogenation reaction of step c) is carried out in the presence of a weak organic or inorganic protic acid such as for example acetic, propionic, butyric, boric acid.

Acetic acid and boric acid are particularly preferred.

Upon termination of the hydrogenation reaction at step c) the residue is treated with aqueous solutions of strong inorganic acids as described in EP 187 345.

A 10% (p/v) solution of HCl is preferred.

An additional advantage of the synthesis process, object of the present invention, is the use of basic reagents such as lower alkyls, from 1 to four carbon atoms, alpha-(hydroxymethyl)acrylates, preferably methyl, ethyl or propyl alpha-(hydroxymethyl)acrylates, more preferably ethyl alpha-(hydroxymethyl)acrylate and phenylacetaldehyde oxime easily available on the market or obtainable according to the description by Villieras J. et Rambaud M. in *Organic Syntheses* 66, pages 220–224 (1988), in *Synthesis*, pages 300–301, (4) (1983), through the synthesis of ethyl alpha-(hydroxymethyl)acrylate, or as described in J. March Advanced Organic Chemistry through the synthesis of phenylacetaldehyde oxime. The stages characterizing the process, object of the present invention, comprise easily realizable reactions with high yields and with standard reagents such as sodium hypochlorite, sodium borohydride, hydrogen and catalysts. In particular, the use of a reducing reagent such as sodium borohydride or sodium dihydro-bis-(2-methoxyethoxy)aluminium hydride ($NaAlH_2(OCH_2CH_2OCH_3)_2$) known as VITRIDE, much less dangerous reagents than other reductants described in literature such as $LiAlH_4$, but however able to achieve excellent yields; The whole combined with the use of basic reagents of low cost and easily available, such as ethyl alpha-(hydroxymethyl)acrylate and phenylacetaldehyde oxime.

According to the tests carried out by the Applicant, the process object of the present invention allows the attainment of 5-benzyl-3-furfuryl alcohol by means of a series of easy-to-do intermediate reactions characterized by yields ranging from over 70% and over 90%, with solvents and reagents commercially available, in mild and easily controllable reaction conditions, starting with basic reagents such as ethyl alpha-(hydroxymethyl)acrylate and phenylacetaldehyde oxime commercially available or which can be synthesized through reactions well known to the art, characterized by high yields, such as those described in the examples reported below.

The reaction products and intermediates were characterized by means of HPLC, TLC, GC and NMR analysis techniques: $^1H$ and $^{13}C$.

Some illustrative, but non-limiting examples of the present invention are described below.

EXAMPLE 1

Synthesis of Ethyl α-(hydroxymethyl)acrylate

In a 1 l capacity reactor are added 96 g (3.2 mol) of p-formaldehyde, 8 ml of orthophosphoric acid ($H_3PO_4$) 1N and 220 ml of $H_2O$. It is heated to 90° C. for 1 h 30 min. At the end, the solution is clear. It is cooled to room temperature and, under strong stirring, are added in order: 60.86 g (0.27 mol) of triethylphosphonacetate, 41.04 g (0.44 mol) of potassium carbonate in 40.56 ml of water. First 10 ml in 10 min, then the rest in 40 min, maintaining the temperature under 35° C.

Once the addition is completed, the solution is allowed to stir at 40° C. for 5 min, then it is quickly cooled to room temperature while in sequence are added 200 ml of ethyl ether and 150 ml of brine (supersaturated solution of sodium chloride). The two phases are separated: the aqueous phase is retroextracted three times, each time with a volume of 150 ml, with ethyl ether, the organic phases are collected, and washed twice, each time with a volume of 150 ml, with brine and are dried with sodium sulphate.

After evaporation of the solvent, 41.55 g of raw ethyl α(hydroxymethyl)acrylate are obtained, which, distilled (70–72° C./1 mmHg), leads to 30.89 g of a colourless liquid product.

EXAMPLE 2

Synthesis of Phenylacetaldehyde Oxime

In a 1 l flask equipped with a mechanical stirrer, two dropping funnels and a thermometer, are added: 33.35 g (0.48 mol) of hydroxylamine hydrochloride dissolved in 69 ml of a 1:2 ethanol/water mixture. Under stirring for 1 h, are simultaneously added dropwise, maintaining the temperature between 10–15° C.: 48.0 g (0.4 mol) of phenylacetaldehyde dissolved in 56 ml of ethanol, 25.44 g (0.24 mol) of sodium carbonate dissolved in 93 ml of water. The formation of a white precipitate is noted 5 min. after starting the addition.

Once the addition is completed the temperature is increased up to room temperature and the solution is allowed to react for 15 h. The precipitate obtained is filtered, washing several times with water. It is vacuum dried for 48 h at room temperature.

49.63 g of phenylacetaldehyde oxime are obtained as a white crystalline solid with a melting point of 84–86° C. 2.05 g of product are recovered from the mother liquors.

EXAMPLE 3

Synthesis of 3-benzyl-5-hydroxymethyl-5-carboxyethyl isoxazoline

In a 1 l flask, equipped with a mechanical stirrer, thermometer and two dropping funnels, are added: 39.0 g (0.3 mol) of ethyl alpha (hydroxymethyl)acrylate in 115 ml of methylene chloride. The solution is cooled to −5° C. and in 4 h are simultaneously added dropwise: 42.0 g (0.3 mol) of raw phenylacetaldehyde oxime, obtained from Example 2, dissolved in 350 ml of methylene chloride, 343 ml of a sodium hypochlorite solution with an active chlorine titre of 10% (titrated before use) equivalent to 0.48 mol of NaOCl. The reaction is slightly exothermic: a temperature rise of about 5° C. is noted; then the dropwise adition is interrupted until the temperature falls to −5° C. The reaction can be checked by gas-chromatography (GC). Once the addition of hypochlorite and oxine is completed, the solution is alowed to stir at room temperature for 2 hr. The two phases that formed are separated: the aqueous phase is retroextracted five times, each time with a volume of 150 ml, of methylene chloride. The organic phases are collected and are washed, first with 200 ml of water, and then twice, each time with a volume of 200 ml, with brine. The organic phase is dried with sodium sulphate. After evaporation of the solvent are obtained 71.55 g of raw 3-benzyl-5 -hydroxymethyl-5-carboxyethyl isoxazoline (95.5% pure, by uncalibrated GC analysis), used as such in the subsequent step.

EXAMPLE 4

Synthesis of 3-benzyl, 5,5-bis(hydroxymethyl)isoxazoline with $NaBH_4$

In a 1 l flask, equipped with thermometer and mechanical stirrer, in a nitrogen atmosphere are added: 71.55 g (0.272 mol) of raw 3-benzyl-5-hydroxymethyl-5-carboxyethyl isoxazoline deriving from Example 3 and 553 ml of methanol. The solution is cooled to −10° C. and in the time period of 1 h are added: 10.29 g (0.272 mol) of $NaBH_4$ granules (10–40 mesh). Once the addition is completed the temperature is increased up to room temperature and the solution is allowed to stir for 1 h 30'. Then are added 250 ml of a saturated ammonium chloride solution maintaining the temperature at approx. 20° C. The solvent is evaporated under vacuum (24 mbar at 25° C.). The residue is taken up with 150 ml of methylene chloride and the residue formed after evaporation is dissolved in a minimum quantity of water. The two phases obtained are separated and the aqueous one is retroextracted three times, each time with a volume of 100 ml, with methylene chloride. The organic phases are collected and dried with sodium sulphate. It is filtered and, after evaporation of the solvent, 59.85 g of a raw orange oil product are obtained. The raw product is crystallized in 150 ml of ethyl acetate and 140 ml of hexane. 39.91 g of 3-benzyl-5,5-bis(hydroxymethyl)isoxazoline as a pale yellow solid are obtained. Another 4.16 g of product are recovered from the mother liquors.

EXAMPLE 4-b

Synthesis of 3-benzyl, 5,5-bis(hydroxymethyl)isoxazoline with sodium dihydro-bis-(2-methoxyethoxy) aluminium hydride ($NaAlH_2(OCH_2CH_2OCH_3)_2$)

Following the same procedure described in example 4, 71.55 g (0.272 mol) of raw 3-benzyl-5-hydroxymethyl-5-carboxyl isoxazoline (95.5% titre) dissolved in 550 ml of methanol are made to react at −10° C. with 80 g (0.272 mol) of 70% (p/p) toluene solution of sodium dihydro-bis-(2-methoxyethoxy)aluminium hydride. The reaction is carried out according to the description in example 4, obtaining 43.3 g of product.

EXAMPLE 5

Synthesis of 5-benzyl-2-hydroxymethyl furane

In a 1000 ml autoclave are added: 50.5 g (0.225 mol) of 3-benzyl-5,5-bis(hydroxymethyl)isoxazoline deriving from Example 4 or from example 4-b, 3.0 g (0.05 mol) of orthoboric acid ($H_3BO_3$), a hydroalcoholic solution of methanol/water in a ratio of 550 ml/110 ml and 5.0 g of Ni raney. The mixture is pressurized at 4 bar of hydrogen and left at this pressure for 8 hours.

The mixture is filtered and evaporated under vacuum (25° C./24 mbar). The residue is treated with dichloromethane and 10% HCl. The organic phase is separated, washed with water and with a brine solution and is afterwards dried on sodium sulphate. It is filtered and the organic phase evaporated under vacuum obtaining an oil that is purified through distillation (125–128° C./0.4 mbar). 35.0 g of 5-benzyl-2-hydroxymethyl furane are obtained (yield 83%).

The invention claimed is:

1. Synthesis process of 5-benzyl-3-furfuryl alcohol comprising the following steps:
    a) condensation reaction of the $C_1$–$C_4$ alkyl alpha-(hydroxymethyl)acrylate with phenylacetaldehyde oxime in the presence of sodium hypochlorite (NaOCl) to give 3-benzyl-5-hydroxymethyl-5-carboxymethyl isoxazoline;
    b) reduction reaction with sodium borohydride ($NaBH_4$) or with sodium dihydro-bis-(2-methoxyethoxy)aluminium hydride ($NaAlH_2(OCH_2CH_2OCH_3)_2$) of 3-benzyl-5-hydroxymethyl-5-carboxymethyl isoxazoline to give 3-benzyl-5,5-bis(hydroxymethyl)isoxazoline;
    c) catalytic hydrogenation reaction of 3-benzyl-5,5-bis(hydroxymethyl)isoxazoline and consequent rearrangement to give 5-benzyl-3-furfuryl alcohol.

2. Process according to claim 1 wherein in the condensation reaction at step a) the alkyl alpha-(hydroxymethyl) acrylate is selected from the group consisting of methyl, ethyl or propyl alpha-(hydroxymethyl)acrylates.

3. Process according to claim 2 wherein the alkyl alpha-(hydroxymethyl)acrylate is ethyl alpha-(hydroxymethyl) acrylate.

4. Process according to claim 1 wherein the condensation reaction at step a) is carried out in aromatic or aliphatic halogenated solvents.

5. Process according to claim 4 wherein the solvents are aliphatic halogenated solvents.

6. Process according to claim 5 wherein the solvents are 1 to 2 carbon atom aliphatic chlorinated solvents.

7. Process according to claim 6 wherein the solvent is methylene chloride.

8. Process according to claim 1 wherein the condensation reaction at step a) is carried out at a temperature of between −10° C. and 80° C.

9. Process according to claim 8 wherein the reaction is carried out at a temperature of between −10° C. and 50° C.

10. Process according to claim 9 wherein the reaction is carried out at a temperature of between −10° C. and 30° C.

11. Process according to claim 1 wherein the condensation reaction at step a) is carried out in the presence of an aqueous solution of sodium hypochlorite with an active chlorine titre of between 5 and 10% p/p.

12. Process according to claim 11 wherein the aqueous solution of sodium hypochlorite has an active chlorine titre of between 8 and 10% p/p.

13. Process according to claim 12 wherein the aqueous solution of sodium hypochlorite has an active chlorine titre of 10% p/p.

14. Process according to claim 1 wherein the reduction reaction at step b) is carried out in a $C_1$–$C_4$ aliphatic alcohol or their mixtures, or in aliphatic or aromatic solvents selected from the group consisting of benzene, toluene, xylene, cyclohexane, methylcyclohexane or mixtures thereof.

15. Process according to claim 14 wherein the alcohol is methyl alcohol.

16. Process according to claim 14 wherein the aromatic solvent is toluene.

17. Process according to claim 1 wherein the reduction reaction at step b) is carried out at a temperature of between −15° C. and 30° C., preferably between −10° C. and 25° C.

18. Process according to claim 1 wherein the reduction reaction at step b) is carried out with sodium borohydride granules (10–40 mesh) in methanol or with sodium dihydro-bis-(2-methoxyethoxy)aluminium hydride in toluene.

19. Process according to claim 18 wherein the reduction reaction at step b) is carried out in a 70% p/p solution in toluene of sodium dihydro-bis-(2-methoxyethoxy)aluminium hydride.

20. Process according to claim 1 wherein the hydrogenation reaction at step c) is carried out at a hydrogen pressure of between 0.5 and 40 bar.

21. Process according to claim 20 wherein the hydrogen pressure is between 1 and 20 bar.

22. Process according to claim 21 wherein the hydrogen pressure is between 1 and 10 bar.

23. Process according to claim 1 wherein the temperature of hydrogenation at step c) is between 15° C. and 100° C., preferably between 20° C. and 60° C.

24. Process according to claim 1 wherein the catalysts used in the hydrogenation reaction at step c) are selected from the group consisting of $PtO_2$, PtO, Ni Raney, Pt on carbon, Pd on carbon, Pd on $BaSO_4$, Pd on $Al_2O_3$, Pt on $Al_2O_3$, Ru on carbon.

25. Process according to claim 24 wherein the catalyst is selected from the group consisting of Pd on carbon, $PtO_2$ and Ni Raney.

26. Process according to claim 25 wherein the catalyst is Ni Raney.

27. Process according to claim 1 wherein the hydrogenation reaction at step c) is carried out in a $C_1$–$C_4$ alcoholic solvent or mixtures thereof, or in hydroalcoholic mixtures of said $C_1$–$C_4$ alcohols, the quantity of water of said mixtures ranging from 7 to 50% v/v of the solution.

28. Process according to claim 27 wherein the alcoholic solvent is methanol.

29. Process according to claim 27 wherein the solvent is a methanol/water mixture with a quantity of water from 10 to 30% v/v.

30. Process according to claim 29 wherein the methanol/water mixture has a water content of 15% to 20% v/v.

31. Process according to claim 1 wherein the hydrogenation reaction of step c) is carried out in the presence of a weak organic or inorganic protic acid.

32. Process according to claim 31 wherein the acid is selected from the group consisting of acetic acid, propionic, butyric, boric acid.

33. Process according to claim 32 wherein the acid is selected out of acetic acid or boric acid.

34. Process according to claim 1 further comprising the treatment of the residue obtained at the end of the hydrogenation reaction at step c) with aqueous solutions of strong inorganic acids.

35. Process according to claim 34 wherein the aqueous solution is a 10% (p/v) solution of HCl.

* * * * *